United States Patent [19]

Swaim et al.

[11] 4,238,198

[45] Dec. 9, 1980

[54] METHOD FOR DETERMINING TOTAL INORGANIC SULFUR

[75] Inventors: Paul D. Swaim; Steven R. Ellebracht, both of Lake Jackson, Tex.

[73] Assignee: The Dow Chemical Company, Midland, Mich.

[21] Appl. No.: 37,810

[22] Filed: May 10, 1979

[51] Int. Cl.³ .................... G01N 21/33; G01N 21/64; G01N 21/73
[52] U.S. Cl. .................. 23/230 R; 23/232 R; 23/232 E; 250/432 R; 422/52; 422/68
[58] Field of Search ............ 250/431, 432 R; 23/230 R, 232 R, 232 E; 422/52, 68, 80

[56] References Cited

U.S. PATENT DOCUMENTS

| | | | |
|---|---|---|---|
| 3,024,182 | 3/1962 | Furth et al. | 250/432 X |
| 3,300,282 | 1/1967 | Risk et al. | 23/232 R |
| 3,770,954 | 11/1973 | Davis | 250/431 X |
| 3,826,920 | 7/1974 | Woodroffe | 250/432 X |

Primary Examiner—R. E. Serwin
Attorney, Agent, or Firm—Burke M. Halldorson

[57] ABSTRACT

A method for the determination of sulfur by which sulfur is reduced to volatile hydrogen sulfide gas and swept into a D.C. plasma where it is detected by vacuum ultraviolet atomic emission spectrometry at 180.7 nm. The method makes possible the determination of trace levels of sulfur in samples where the matrix would normally result in spectral and/or chemical interferences.

10 Claims, 8 Drawing Figures

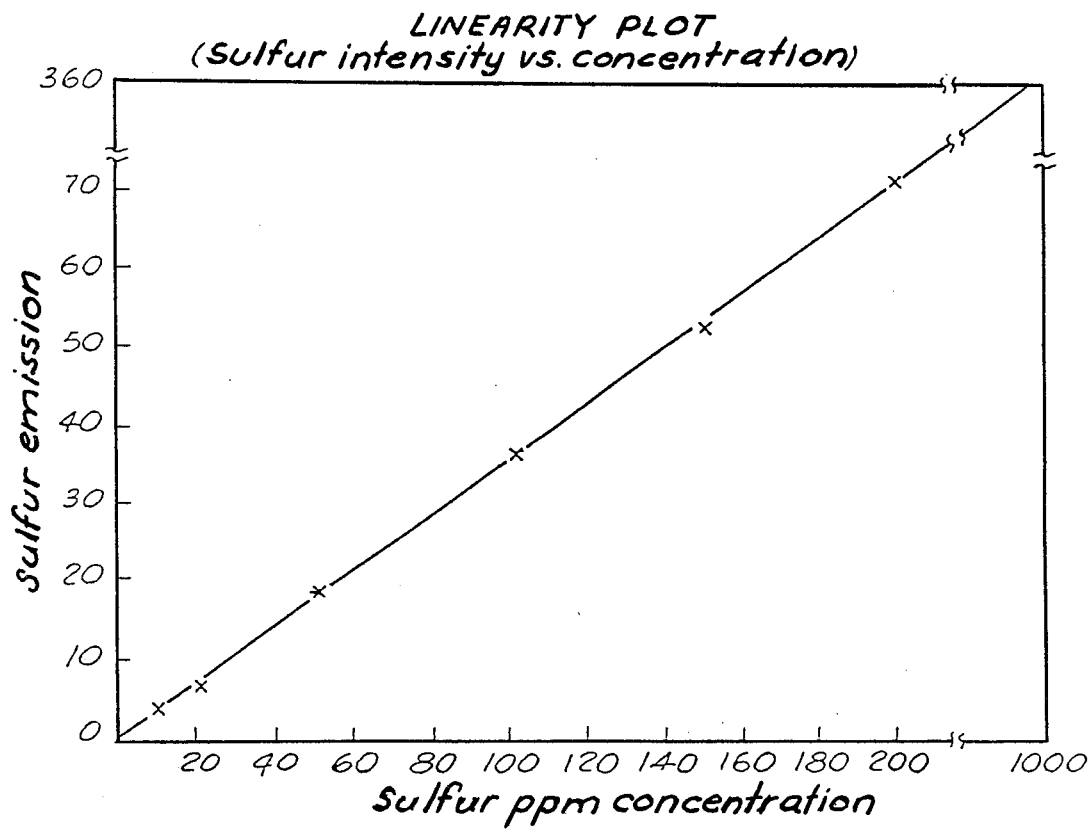
FIG. 6
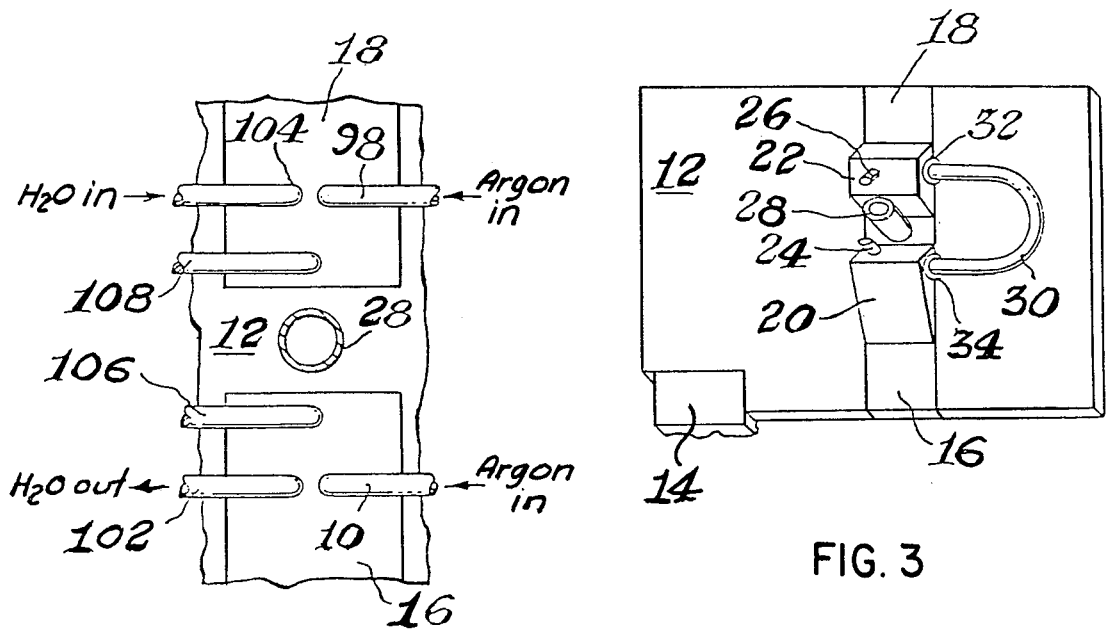
FIG. 4
FIG. 3

METHOD FOR DETERMINING TOTAL INORGANIC SULFUR

FIELD OF THE INVENTION

The invention relates to the field of elemental analysis wherein sample is atomized and excited by a plasma, and the emitted light analyzed to determine concentration. More particularly, the invention relates to an improved method for quantitatively analyzing samples to determine total inorganic sulfur.

BACKGROUND OF THE INVENTION

Quick and reliable methods for the determination of trace levels of sulfur in a wide variety of sample matrices have long been pursued by the analytical chemist. As with many nonmetallic elements, sulfur has not proven easily amenable to detection of microgram and sub-microgram quantities. This has been further complicated by the fact that techniques for separating and/or concentrating sulfur at these levels are sometimes cumbersome. The result is that, at best, methods for determining traces of sulfur usually are tedious and require considerable operator time and skill.

As a specific example, there exists a need for an improved method for routinely determining sulfur in a salt matrix in the range of 0.5 to 100 ppm. Existing titrimetric or colorimetric methods are found to be either insufficiently sensitive for this determination or excessively time consuming. Known turbidimetric and polarographic methods are also found disadvantageous due to lack of specificity and/or reproducibility. Known instrumental techniques which have been before used to determine sulfur include X-ray fluorescence, neutron activation, and charged-particle activation analysis, but these oftentimes either are not adequately sensitive or, in cases, would be impractical.

Consequently, a fast and highly sensitive method of good specificity and reproducibility, for determining total inorganic sulfur, would represent a highly desired advance in the state of the art.

SUMMARY OF THE INVENTION

An improved method for analyzing liquid samples for total inorganic sulfur, and which avoids many of the prior difficulties, comprises introducing the sample into a reducing solution effective to reduce inorganic sulfur of said sample to H$_2$S, sweeping the volatile H$_2$S evolving from the reducing solution using an inert carrier gas and ultimately in-line to a plasma, wherein the evolved H$_2$S is atomized and excited by the plasma, and analyzing the emitted light resultingly attained to determine total inorganic sulfur concentration.

Most preferably, the sample is analyzed by means of vacuum ultraviolet atomic emission spectrometry at 180.7 nm, or alternately at 182.0 or 182.6 nm. Preferred apparatus for performing such analysis, and which minimizes the effects of oxygen absorption, utilizes a dynamic gas blanketing technique wherein purging gas is continuously formed about the plasma, and which gas is non-absorbing of light in the sub-200 nanometer wave length range. The purging gas used to form the blanket, and also the carrier gas used to bring the H$_2$S into or in to a region immediately adjacent the plasma, is most preferably argon in each case.

Other gases having suitable characteristics, for exemplary purposes only, include any and all of the remaining noble gases, together with nitrogen and/or mixtures of the above. Argon or one of the remaining noble gases, e.g., helium, is similarly preferred for generating the plasma. Where plasma stability permits, it is possible to use the same gas, e.g., argon, for generating the plasma, as the carrier gas, and for purging. Otherwise, a distinct plasma gas may be required.

The preferred reducing solution for use in the invention is prepared by admixing hydriodic acid, hypophosphorus acid, and an iodide ion contributing source most effectively potassium iodide. A solution found to perform best is made up according to the following range:

| Material | Amount |
|---|---|
| 55–58% by weight aqueous hydriodic acid | 25–35 mls |
| 50–52% by weight aqueous hypophosphorus acid | 10–20 mls |
| Reagent grade potassium iodide | 25–35 grams |

The solution most preferably used comprises 30 ml of hydriodic acid which is 55–58 percent by weight, 15 ml of hypophosphorus acid which is 50–52 percent by weight, and 30 grams of reagent grade potassium iodide.

More generally, the solution is made acidic preferably using hydriodic and hypophosphorus acids preferably using quantities such as stated above. It also contains a reducing ion, such as I$^-$, preferably made from reagent grade potassium iodide and hydriodic acid in the above stated quantities. Iodine (I$_2$) is simultaneously reduced to iodide (2I$^-$) preferably by hypophosphorus acid using the above concentrations.

The reduction step is performed using the above reducing solution maintained at or near boiling temperatures, i.e., within the range generally of about 90° C. to about 120° C., and, preferably, under the further condition of maximum agitation of the solution. The most preferred temperature range, for the specific solution, supra, is from about 105° C. to about 115° C.

THE DRAWING

The invention is further disclosed in reference to the preferred embodiment by the following more detailed description, taken in conjunction with the accompanying drawing wherein:

FIG. 3 is an isometric view showing certain of the interior detail of the purge chamber section of the FIG. 1 apparatus.

FIG. 4 is a bottom partial view of the purge chamber illustrating the service connections to the plasma source.

FIG. 6 is a reproduction of a graph comprising a calibration curve.

DETAILED DESCRIPTION OF THE INVENTION

Figure 1:
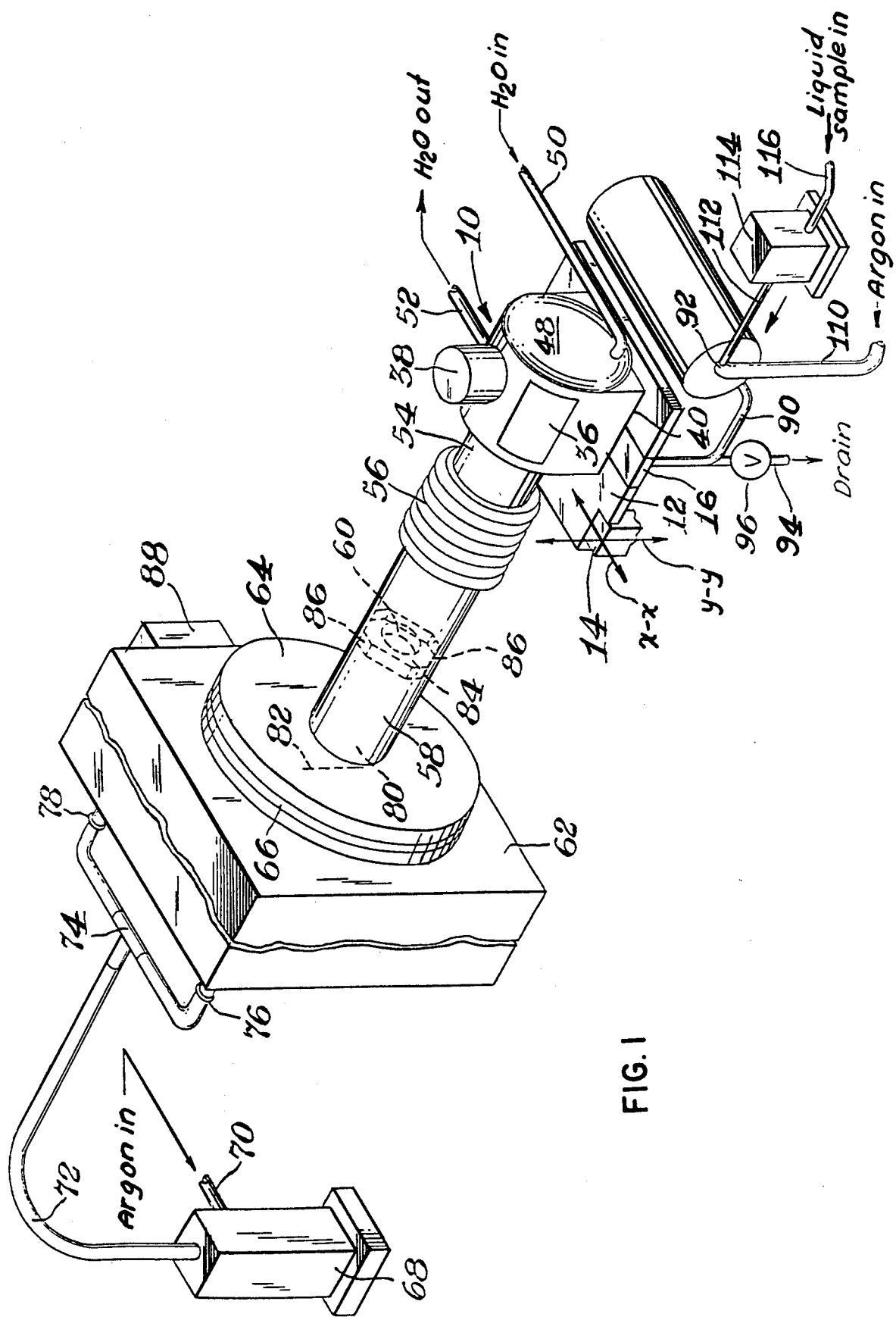
FIG. 1 is an isometric view of a preferred embodiment of a vacuum ultraviolet (VUV) plasma atomic emission spectroscopic instrument designed for use in the method of the present invention.
Figure 2:
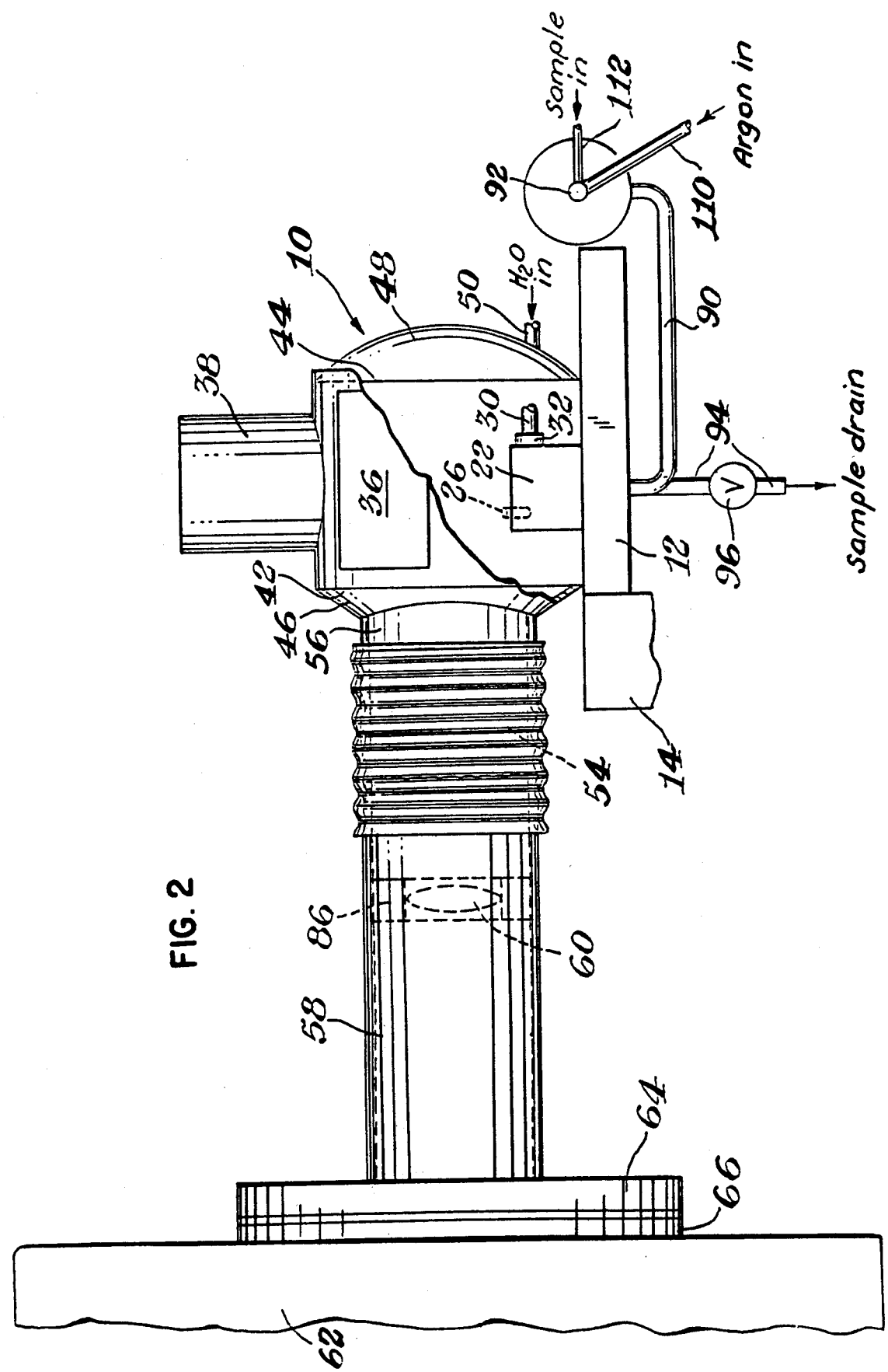
FIG. 2 is a side elevational view of the apparatus of FIG. 1.

Referring to the drawing, and most particularly, FIGS. 1 and 2, the VUV plasma atomic emission spectroscopic instrument or apparatus illustrated comprises an enclosed plasma purge chamber designated generally by reference numeral 10. The plasma purge chamber is seated on a flat base member or base 12 which is mounted for translational movement in the direction of the x—x and y—y axis on a standard optical alignment device shown partially at 14, and preferably, comprising a combination Model 22-4071 and 22-4089 from Ealing Optics. Base 12 preferably comprises a machinable, hardened, high density fiberglas material. Inset in base 12, as shown best in FIG. 3, are a pair of filler blocks 16 and 18, preferably of the same fiberglas material. Attached to the base in the space between the filler blocks are a pair of spaced electrode holders or holder blocks 20 and 22. Mounted in holders 20 and 22, respectively, are ceramic sleeves 24 and 26. Disposed coaxially within the latter are preferably tungsten electrodes (not shown) which cooperate with sleeves 24 and 26 to generate a plasma. The electrodes, in the preferred design, converge together in the known V geometry. Disposed in between the electrodes is a sample introduction means or aerosol chimney 28 (see FIGS. 3 and 4) through which aerosol or gaseous sample is admitted, and dispersed in or near the region of the plasma. The holder blocks 20 and 22 are water cooled, by means of a conduit of flexible tubing 30, preferably or polyvinyl chloride affixed between the blocks by means of brass fittings 32 and 34. The arrangement of the plasma jet or plasma, i.e., elements 20 through 30, are known and described in U.S. Pat. No. 4,009,413, the teachings of which are herein incorporated by reference. Commercial plasma sources made under the teachings of this patent are commercially available from SpectraMetrics, Incorporated, Andover, Massachusetts.

The purge chamber is preferably of stainless steel and includes a cobalt viewing glass 36. The geometry is preferentially generally hemispherical to assist smooth gas flow through the system. Centered over the plasma source is a purge vent 38 which operates by draft principles.

Most preferably, the lower lip 40 of the purge chamber is machined to a high degree of smoothness in order to seat flushly with base 12, without requiring physical attachment. Thus, the purge chamber may be conveniently removed for servicing. Alternately, the preferred embodiment contemplates a hingedly attached and thus pivotally removable purge chamber. The middle section of the chamber, i.e., as defined between spaced weld lines 42 and 44 and not critically including vertical side portions 46 and 48, embodies most preferably a double wall construction, thus forming a water cooling jacket through which cooling water is circulated via water inlet hose 50 and outlet hose 52.

The side portion 46 is joined rigidly to a sleeve 54, such as by welding, the latter being also most preferably of stainless steel. Sleeve 54 defines an internal passage or port means that is aligned with the centerline of the purge chamber (at least one port means is employed, although several may be employed in alternate and satisfactory designs). A flexible tube element, preferably a paper flex tubing 56, is fitted at one end over sleeve 54, and at its other end, over an elongated purge tube or hollow connector or connector element 58 constructed such as transparent Plexiglas, but which alternately, may be coated with black paint to minimize reflection. Preferred tube dimensions are noncritically, 5 cm O.D., 4.4 cm I.D., and 12 cm axial. The flex tube cooperates with translational device 14 for adjusting the optical alignment between the plasma source, a biconvex lens element or light focusing means 60 mounted interiorly of purge tube 58, and a monochromator 62 affixed to the purge tube by a flange coupling 64 and seating gasket 66. The preferred embodiment uses a vacuum operated type, Model 218, McPherson monochromator. Since the model designated is adapted for internal evacuation, it is readily suited to compatibly incorporate the modifications below.

These modifications include the addition of a gas flow meter or regulator 68 (preferably a size 2-4-65A, from Brooks Instrument Division, Emerson Co.), adjustable between flow rates of 1–10 standard cubic feet per hour. An incoming pressurized purge gas line 70 into the gas flow regulator provides pressurized gas, which is outfed through outgoing line 72 to a t-fitting 74. The fitting routes the gas to a pair of spaced inlet ports 76 and 78, of the monochromator, the latter provided in the above-designated commercial device. Ultimately the infeed gas emerges from the forward entrance 80 of the monochromator in communication with purge tube 58. Inside forward entrance 80 is an optical light transmission slit, shown and represented by dotted line 82.

The purging technique critically requires the introduction into the monochromator of a controlled gaseous environment maintained continuously from the plasma source to a suitable detector, e.g., a photomultiplier tube 88 attached to monochromator 62, and preferably comprising a Model 9783B Photomultiplier tube from EMI Gencom, Inc. To this end, lens 60 is mounted in a holder element 84 which is adapted to form passageways 86, for continuous gas flow past the obstruction of the lens. The lens most preferably is 1" in diameter and constructed of Supersil II, from Acton Research, Acton, Massachusetts.

Referring to further details of the instrument, the monochromator is preferably further modified by coating all mirrors and the grating element with a thin coating of $MgF_2$ in order to minimize light absorption in the higher energy region of the spectrum, this fabrication being available from Acton Research. Further, in respect to the preferred detail of base 12, various line connections are brought to and through the bottom of the base to service the plasma source (see also FIG. 4). These include a Tygon tube 90 communicating between a nebulizer 92 (See FIG. 1) and aerosol chimney 28. Tube 90 includes at an intermediate section, connection to a drain tube 94 through a normal open restrictor valve 96. Further service inlets include gas or plasma gas inlets 98 and 100 connected to electrode sleeves 22 and 24, and supplying plasma source gas to the electrodes. In addition, water inlet and outlet lines 102 and 104 are shown for water cooling mounting blocks 20 and 22, and DC electrical connection lines 106 and 108 for energizing the tungsten electrodes.

Figure 5:
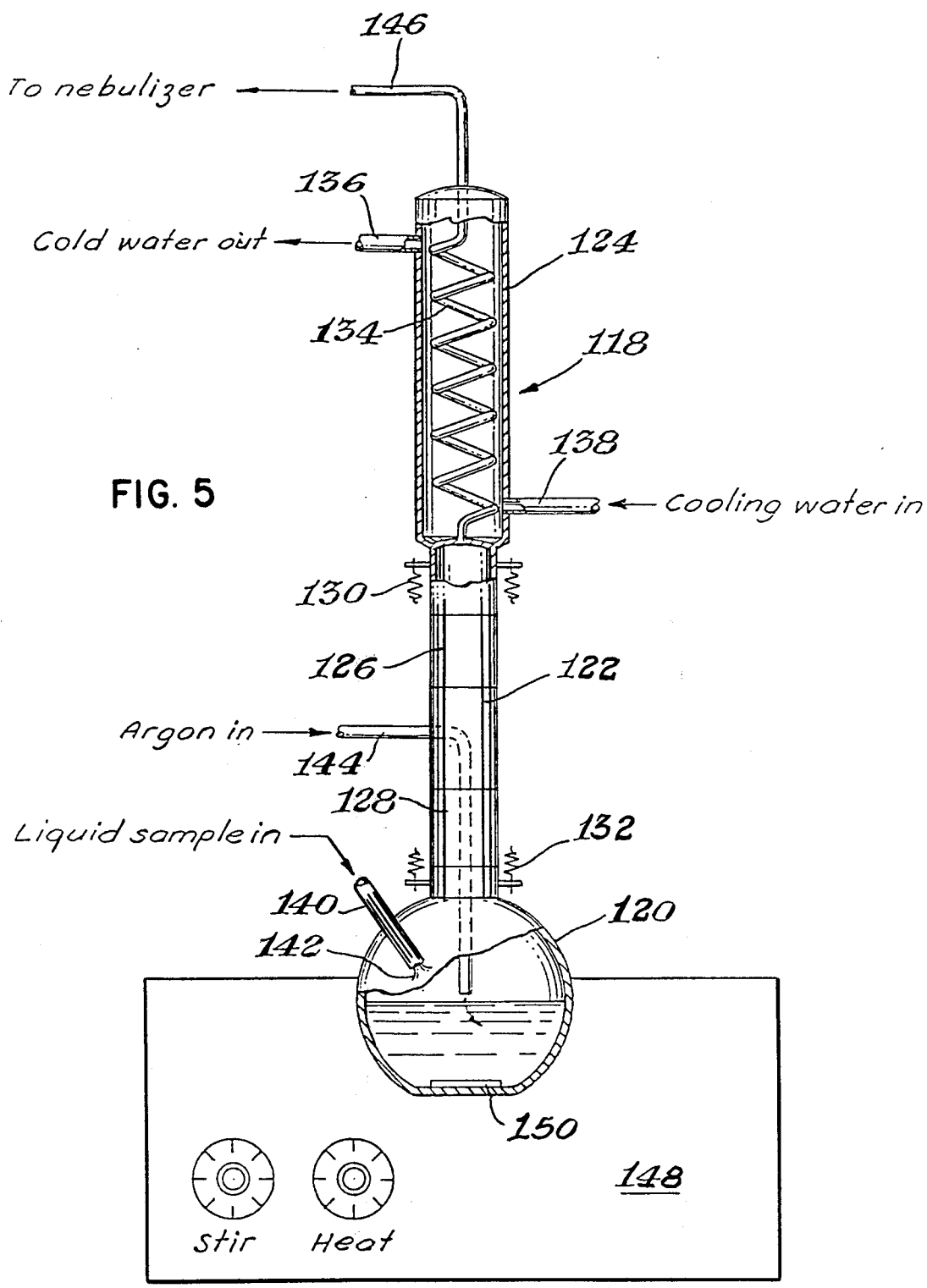
FIG. 5 is a side elevational view showing the preferred form of apparatus for reducing inorganic sulfur to hydrogen sulfide gas.

The nebulizer, in detail, includes further connection to a gas inlet line 110, and a sample inlet line 112, the latter connecting to a peristaltic pump 114, preferably a catalog No. 53202, from SpectraMetrics. The peristaltic pump receives sample from a beaker (not shown)

through a line connection 116, or alternatively from a gas generating or evolving device shown separately in FIG. 5, and described below, with respect to the Example Series II.

OPERATION/DIRECT LIQUID SAMPLE ANALYSIS

Sample in liquid or liquefied form, preferably in water or a known organic solvent system suitable for use in the field of the invention, is advanced by peristaltic pump 114 to nebulizer 92. Argon gas at a controlled flow rate of preferably between about 2–5 standard cubic feet per hour is simultaneously routed to the nebulizer through line connection 110. The nebulizer resultingly mixes the sample with argon, producing a sample aerosol in argon gas that is ultimately introduced between the tungsten electrodes through nebulizer chimney 28. Argon gas through plasma source inlets 98 and 100 is simultaneously supplied through the annular space defined between the electrodes and sleeve elements 22 and 24, the operation of the electrodes being under sufficient energy to produce a hot plasma of ionized argon gas, into which the aerosol sample is dispersed. Preferred flow rate through the sleeve member is controlled within the range of about 2–4 standard cubic feet per hour. Operating temperature of the plasma is estimated at about 6000° C.–10000° C. The plasma is heated sufficiently to cause excitation of the element or elements of interest in the sample. The light emitted by the excitation of the sample is focused by means of lens 60 onto the light transmission slit of the monochromator which resolves the wave lengths of interest for ultimate detection by the photomultiplier tube in the known manner. The photomultiplier tube is preferably used in conjunction with a current amplifier and current to voltage converter to process the light signal and thus allow recording of the results on a strip chart recorder in the known manner. This is then used to generate the data.

The improvement in operation is realized by means and provision of the purge system. In this respect, preferably argon introduced under pressure into the monochromator, via gas flow meter 68 and connections 76 and 78, is routed internally of the monochromator such that the emitted light passes only through the controlled purge atmosphere thus created. The gas exits from the monochromator through purge tube 58, about lens holder 84, and into purge chamber 10. Argon from this source, and all sources in the system, and the sample aerosol is removed by draft through vent 38. It is understood that the purging gas most desirably flows and sweeps continuously through all areas through which the emitted light travels ultimately to detector 88 (including purging of the detector casing). Consequently, a steady state atmosphere is created by which means it is possible to negate the effects of oxygen absorption, in the 160–200 nm band, in a manner which uniquely achieves excellent sensitivity and reproducibility of data.

The invention is further characterized over known prior systems in terms of capabilities as shown in the examples below.

EXAMPLE SERIES I/DIRECT LIQUID SAMPLE ANALYSIS

Using the instrument design of the preferred embodiment, comparative analysis tests are run using established wet chemical methods to determine the relative reproducibility and accuracy of the plasma purge VUV instrument of this invention. In these experiments, the instrument is initially purged with argon for ten minutes before running samples (to rid the system of the effects of oxygen absorption). Samples can then be run in one- to two-minute intervals. The analysis procedure consists of diluting 34 weight percent $MgCl_2$ one to two, and 68 weight percent $MgCl_2$ one to four by weight in water. The samples are then aspirated directly into an argon plasma. The sulfur emission is recorded as a steady state rise in signal level above background and is measured against sulfur standards prepared in "sulfur-free" 17 percent $MgCl_2$. The experiments of this Example series employ the following instrument settings:

| Monochromator: | |
|---|---|
| Entrance | 25μ |
| Exit | 25μ |
| Wave length: | 180.7 nm |
| Argon Flow: | |
| Aspirator | 5 SCFH |
| Plasma | 4 SCFH |
| Purge | 3.5 SCFH |
| Same Aspiration Rate | 2 ml/min |
| PMT Voltage | 800 |

The short-term precision data is shown in Table I. Typically, the precision is within 4 percent relative standard deviation. A calibration curve generated from sulfur made up in 17 percent $MgCl_2$ is shown to be linear up to at least 1000 ppm sulfur (FIG. 6). Accuracy is determined by running ten samples of 34 percent and 68 percent $MgCl_2$ using the described VUV instrument and comparing these results with those previously obtained using reliable wet chemical analytical procedures. More specifically, the analysis is compared with data obtained using the wet chemical methods described by Archer, Analyst, 81, 181 (1956). Although somewhat lengthy, the latter prior art procedure has been routinely used for a number of years and found to be reliable for quantities of sulfur in the 100–300 μg range. The accuracy results are summarized in Table II.

TABLE I

Short-term Precision of the Determination of Sulfate (as Sulfur) in 17 Percent Magnesium Chloride

| | *ppm $SO_4^=$ (34% $MgCl_2$) | *ppm $SO_4^=$ (68% $MgCl_2$) |
|---|---|---|
| | 377 | 391 |
| | 377 | 400 |
| | 389 | 400 |
| | 389 | 400 |
| | 394 | 391 |
| | 377 | 400 |
| | 389 | 400 |
| | 394 | 400 |
| | 377 | 396 |
| | 389 | 400 |
| Average | 385 | 398 |
| Relative % Std. Deviation | 3.8% | 2% |

*The two sets of data represent two different samples.

TABLE II

Accuracy in the Determination of SO$_4^=$ (as Sulfur) in 34% and 68% MgCl$_2$

| Sample Nos. | Wet Chemical ppm SO$_4^=$ | Plasma Purge ppm SO$_4^=$ |
|---|---|---|
| 34% MgCl$_2$ | | |
| B' Pl 4/9 | 400 | 390 |
| B600 4/8 | 390 | 380 |
| B600 4/7 | 390 | 394 |
| A600 4/7 | 460 | 457 |
| B600 4/9 | 400 | 396 |
| A600 4/8 | 340 | 352 |
| B' 600 4/8 | 390 | 384 |
| A' 600 4/8 | 340 | 354 |
| A' 600 4/7 | 460 | 449 |
| B 4/9 | 400 | 428 |
| 68% MgCl$_2$ | | |
| 4/4 FBD-2 | 580 | 525 |
| 4/5 CF-B | 398 | 393 |
| 4/10 CF-B | 420 | 405 |
| 4/3 CF-B | 390 | 398 |
| 4/8 CF | 360 | 377 |
| 4/8 FBD-2 | 390 | 405 |
| 4/7 CF-B | 400 | 388 |
| 4/9 CF-B | 370 | 388 |
| 4/7 FBD-2 | 520 | 476 |
| 4/8 T-31 | 4590 | 4397 |

The data of Table II illustrates, in these experiments, an accuracy compared with the identified wet chemical procedure of within 4 percent average relative deviation. The data is generated at a rate of about 2 minutes per sample, compared to about 20 minutes per sample for the wet chemical method. The improvement based on the plasma purge is, in addition, ideally suited to determination in the parts per million range of such difficult elements (in addition to sulfur) as phosphorus, arsenic, selenium, mercury, iodine and carbon. More generally, the instrument is ideally suited to analysis of elements having strong atomic emission lines in the region between about 160–200 nanometers, as well as in the more general range above 200 nanometers.

EXAMPLE SERIES II/GAS EVOLUTION

Most advantageously, the invention here is practiced with respect to the analysis of sulfur in sample matrices including high concentration of various salts. More specifically, the invention employs a gas generating or evolution apparatus as shown in FIG. 5, and designated generally by reference numeral 118. Apparatus 118 comprises a flask section 120, a gas inlet adapter section 122, and a condenser section 124. The three sections are joined together by ground glass joints 126 and 128, and held by retaining springs 130 and 132.

A seven-turn spiral condenser 134, cooled by water circulated through water inlet, outlet connections 136, 138 is used to ensure complete condensation of the evolved vapors. A septum support 140 is connected to the boiling flask (250 ml) by means of a $\frac{1}{4}''$ O.D. glass stem 142. The stem is angled so that an injected sample strikes the solution rather than a gas inlet tube designated 144. The heating flask is adapted to be heated and stirred preferably by means of an electrothermal agitator 148 and bar stirrer 150, from Electrothermal Engineering Limited, London, England.

The gas evolution apparatus is connected to VUV instrument by disconnecting the previously described argon line 110 from nebulizer 92, which is then connected to argon inlet 144 of the FIG. 6 apparatus. In conjunction, the evolved sample outlead line, designated 146, is connected to nebulizer 92 in the manner previously occupied by line 110.

A solution ideally used for the reduction of sulfur comprises 30 grams of potassium iodide, 30 ml of hydriodic acid (55–58 percent by weight), 15 ml of hypophosphorus acid (50–52 percent by weight), and is contained in flask 120.

Using the modification of this Example Series II, the analysis of high salt samples may be advantageously performed with no special sample preparation. In performing such analysis, the flask is heated to boiling temperature. Sample in solution is injected into the flask through septum mount 140. Assuming the described reducing solution and a sulfur-containing sample, the sample upon contacting the hot reducing solution causes the sulfur to be reduced to H$_2$S gas. The salts are separated and remain in the reducing solution. The evolved gas is swept out by argon through the condenser coil, and into the nebulizer for subsequent analysis according to the technique as described, supra.

The data of this experiment uses the preferred following apparatus parameters.

| Gas Evolution Apparatus: | |
|---|---|
| Flask Heating Temperature | 105° C.–115° C. |
| Stirring Rate | 1050–1100 RPM (with standard 1-inch stirring bar) |
| Argon Flow Rate | 2–4 SCF/Hr |
| VUV Instrument Parameters: | |
| Electrode Current | 7 amperes |
| Slit Widths | 25 μm entrance 25 μm exit |
| Argon Flow Rates | |
| Plasma Source | 2 SCFH |
| Nebulizer | 4 SCFH |
| Purge | 3 SCFH |
| Analytical Wave length Setting | 180.7 nm |

ACCURACY OF METHOD

Three high salt samples (approximately 20 percent KCl; 20 percent MgCl; 20 percent NaCl; 15 percent CaCl), each with varying sulfur content, are analyzed according to the invention, and the analysis is compared with data obtained using the wet chemical methods described by Archer, Analyst, 81, 181 (1956). The results given in Table III show good agreement between the methods.

TABLE III

| | Accuracy,[a,b] | | |
|---|---|---|---|
| | Sample No. 1 | Sample No. 2 | Sample No. 3 |
| Titrimetric | 93.2 ± 0.5 | 96.7 ± 0.3 | 103.2 ± 1.0 |
| Present Method | 95.3 ± 0.4 | 97.3 ± 0.8 | 105.3 ± 1.0 |

[a]Results given as mean of triplicate determinations.
[b]Results in parts per million.

REPEATABILITY OF METHOD

Repeatability is determined by performing 10 consecutive analyses of a 20 percent w/v solution of salt sample known to contain a small amount of sulfur. Each determination is performed by injecting 100 μl of a 20 μg/ml standard solution, followed by 100 μl of the sample solution. The concentration of sulfur in the salt sample is calculated, and from these results a relative standard deviation is derived, the results being given in more detail in Table IV, below.

TABLE IV

| Analysis | Repeatability | | Concentration of Sulfur[2] |
|---|---|---|---|
| | Sample Peak Height[1] | Standard Peak Height[1] | |
| 1 | 70 | 138 | 50.7 |
| 2 | 72 | 143 | 50.3 |
| 3 | 75 | 148 | 50.7 |
| 4 | 74 | 147 | 50.3 |
| 5 | 71 | 145 | 49.0 |
| 6 | 74 | 150 | 49.3 |
| 7 | 76 | 148 | 51.4 |
| 8 | 81 | 154 | 52.6 |
| 9 | 79 | 153 | 51.6 |
| 10 | 77 | 152 | 50.7 |
| | | X = | 50.6 |
| | | S = | 1.06 |
| | | RSD = | ±2.1% |

[1]Expressed in millimeters.
[2]Concentration in parts per million.

A relative standard deviation of ±2.1 percent shows that the technique has very good short-term reproducibility. Further examination of the data reveals that over the period of time required to perform this series of analyses (about 45 minutes), sensitivity appears to vary somewhat. This can readily be seen from the values of peak heights for the standards, which varied from a low of 138 mm to a high of 154 mm, representing a change of slightly over 10 percent. It has been observed that the plasma excitation source used in this instrument is not stable over a long period of time, believed mainly due to aging of the electrodes. However, changes which occur usually do so gradually. In practice, it has been found that if standards are thus run every third sample, the results will be within 5 percent relative error of the true value.

TEMPERATURE, STIRRING RATE, AND NEBULIZER FLOW RATE

Figure 7:
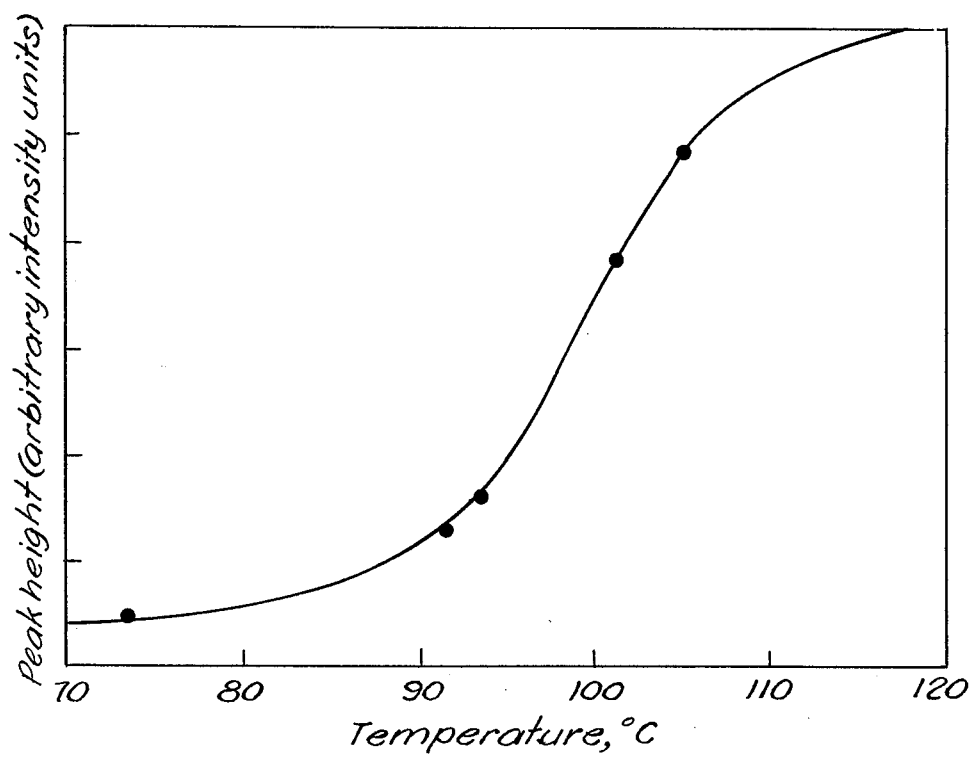
FIGS. 7 and 8 are further graphs pertinent to the detailed description of the invention, below, and generally showing the effect of temperature and stirring parameters on the rate of reduction of inorganic sulfur to H₂S.

The effect of temperature on the evolution of hydrogen sulfide is illustrated in FIG. 7. The greatest sensitivity in terms of peak height is achieved at temperatures above 110° C. Peaks obtained at temperatures below about 90° C. are broad and ill-defined, indicating a slow rate of evolution.

Figure 8:
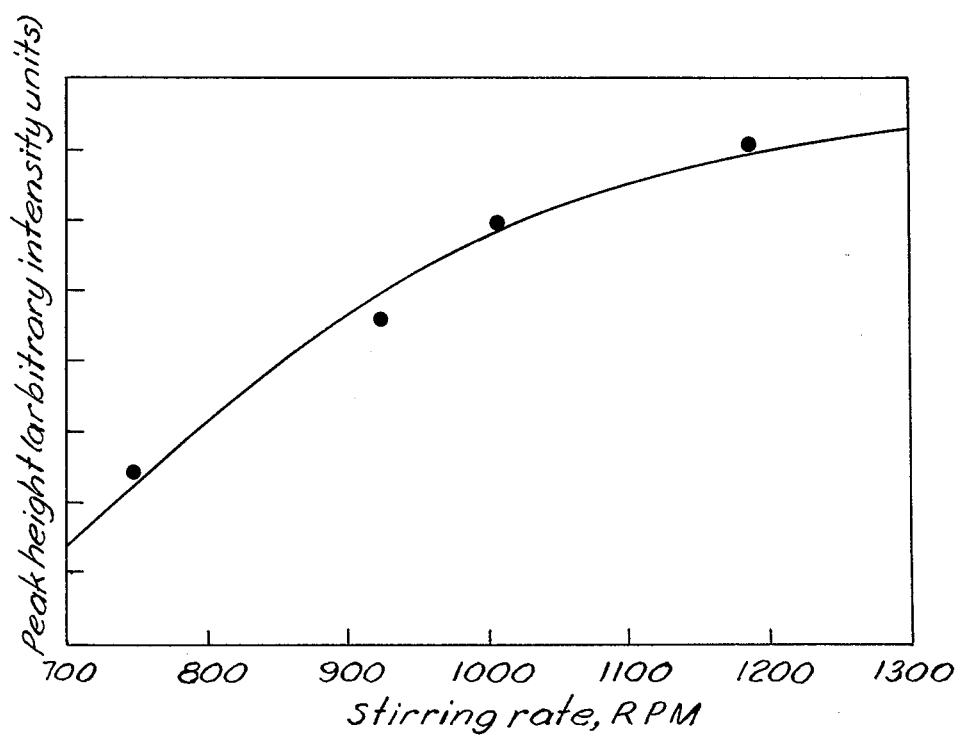

As can be seen from FIG. 8, peak height (i.e., rate of evolution) varies almost directly with stirring rate up to about 1100 rpm. In practice, stirring rates as high as possible are found to give the best sensitivity and most reproducible results.

The rate of hydrogen sulfide evolution is found to be dependent upon the nebulizer flow rate because of the cooling effect the flowing argon stream exerts on the reducing solution. In general, lower flow rates result in higher temperatures and thus a higher rate of evolution. However, flow rates much below 4 SCFH may result in distortion and instability of the plasma, and therefore a decrease in the signal-to-noise ratio. A nebulizer flow rate of 3.5 to 4 SCFH is thus considered to be the best compromise.

EFFECT OF FORMS OF SULFUR

Since inorganic sulfur occurs in a wide variety of chemical forms and oxidation states, it is desirable to know if the form of sulfur may affect the rate of evolution of hydrogen sulfide. This is done by injecting consecutive 100 μl aliquots of solution which contain 10 μg/ml of sulfur in the following forms: sulfate, sulfite, persulfate, thiosulfate, dithionate, thiocyanate, and aqueous hydrogen sulfide. The data, given in Table V, shows that each form of inorganic sulfur results in about the same peak height within the limits of long-term reproducibility of the technique. This suggests that the limiting factor for the rate of evolution is the rate at which hydrogen sulfide can be stripped from the solution. It is not believed due to a slow rate of reduction, since aqueous hydrogen sulfide yields the same peak height as other inorganic forms of sulfur. This fact greatly simplifies the analytical procedure, since it is unnecessary to convert all the various inorganic forms of sulfur to a single state prior to analysis.

TABLE V

Effect of Form of Sulfur on Peak Height

| Sulfur Species | Peak Height[1] |
|---|---|
| Sulfate | 92 |
| Sulfite | 96 |
| Thiocyanate | 87 |
| Persulfate | 93 |
| Thiosulfate | 90 |
| Dithionate | 95 |
| Hydrogen Sulfide, Aqueous | 90 |

[1]Expressed in millimeters.

INTERFERENCES

Chemical interferences in the reducing solution can likely occur via two modes of action: (a) the species might react with sulfide and inhibit the evolution of hydrogen sulfide, or (b) the species might react with the reducing solution and possibly hinder the reduction of sulfur. These possibilities are investigated by spiking a solution of a possible interfering species with a known amount of sulfur and comparing the peak height to that obtained from a standard sulfur solution. The results, given in Table VI, show that strong oxidants do not apparently affect the evolution of hydrogen sulfide, even though reducing agent is consumed. Cations which form acid-insoluble sulfides also do not appear to interfere. However, a high concentration of sodium hydroxide results in a reduction in peak height of about 16 percent. The interference is apparently not due to the consumption of acid, as subsequent injections of standard sulfur solution do not show a similar reduction in peak height. No reason can be advanced for this behavior. An even greater reduction of peak height is observed with ammonia, but this is the result of a thick cloud of ammonium iodide which accompanied the hydrogen sulfide into the plasma. Therefore, the interference is optical in nature rather than chemical.

TABLE VI

Effects of Possible Interferences

| Solution[1,2] | Peak Height[3] |
|---|---|
| $H_2O$ | 85 |
| $HNO_3$, 7% | 86 |
| $H_2O_2$, 3% | 84 |
| $Pb(NO_3)_2$, 2% | 88 |
| $HgCl_2$, 2% | 89 |
| NaOH, 10% | 71 |
| NaOH, 2% | 87 |
| $NH_3$ (aq), 2% | 48 |

[1]Concentration of interferent is on weight/volume basis.
[2]All solutions 20 μg/ml sulfur in the form of sulfate.
[3]Expressed in millimeters.

CAPACITY OF THE REDUCING SOLUTION

The reducing power of the solution may be eventually weakened if repeated injections result in increase in volume and dilution of the mixture. It has been observed, however, that significant increases of volume do not occur, probably because of gradual losses which result from incomplete condensation of water and hydriodic acid. Although not having actually exhausted a solution, it is observed that as long as samples are non-basic and relatively free of oxidants, several hundred injections of 100 $\mu$l each can be made over a period of about 3 weeks without any apparent loss of quality.

What is claimed is:

1. An improved method for analyzing liquid samples for total inorganic sulfur, and which comprises: introducing the sample into a reducing solution which is effective to reduce inorganic sulfur of said sample to $H_2S$ sweeping the volatile $H_2S$ evolving from the reducing solution using an inert carrier gas and ultimately in-line to a plasma, and wherein the evolved $H_2S$ is atomized and excited by the plasma, and analyzing the emitted light resultingly attained to determine the total inorganic sulfur concentration of said sample.

2. The method of claim 1 comprising the use therein of an aqueous based reducing solution prepared from hydriodic acid, hypophosphorus acid, and an iodide ion contributing compound, the ingredients being in proportions effective to reduce inorganic sulfur to $H_2S$.

3. The method of claim 2 including the step of heating the reducing solution to a temperature of between about 90° C. to about 120° C.

4. The method of claim 3 wherein the iodide ion contributing compound comprises potassium iodide.

5. The method of claim 4 including the step of continuously agitating the reducing solution.

6. The method of claim 5 wherein the $H_2S$ is detected by VUV atomic emission spectrometry in the sub-200 nanometer wave length range.

7. The method of claim 6 wherein the $H_2S$ is detected at 180.7 nanometers.

8. The method of claim 7 wherein the evolved $H_2S$ is swept through a gas condenser prior to being swept to said plasma.

9. The method of claim 8 wherein the carrier gas is selected from the group of noble gases, nitrogen, and mixtures thereof.

10. The method of claim 9 wherein the carrier gas comprises argon.

* * * * *

UNITED STATES PATENT AND TRADEMARK OFFICE
CERTIFICATE OF CORRECTION

PATENT NO. : 4,238,198
DATED : December 9, 1980
INVENTOR(S) : Paul D. Swaim and Steven R. Ellebracht It is certified that error appears in the above—identified patent and that said Letters Patent is hereby corrected as shown below:

Col. 3, line 33, delete the word "or" and insert --of--.

Col. 6, line 25 (Example Series I), delete the word "Same" and insert --Sample--.

Col. 9, last column of Table IV, Item 7, move the figure "51.4" to the right so that it is in line under the rest of the column.

Col. 11, line 2, delete "increase" and insert --increases--

Col. 11, Claim 1, line 21, insert a comma --, -- first occurrence after "$H_2S$".

Signed and Sealed this

Seventh Day of April 1981

[SEAL]

Attest:

RENE D. TEGTMEYER

Attesting Officer     Acting Commissioner of Patents and Trademarks